(12) United States Patent
Gokaraju et al.

(10) Patent No.: US 7,741,370 B2
(45) Date of Patent: Jun. 22, 2010

(54) DOUBLE SALTS OF (−)-HYDROXYCITRIC ACID AND A PROCESS FOR PREPARING THE SAME

(75) Inventors: Ganga Raju Gokaraju, Andhra Pradesh (IN); Rama Raju Gokaraju, Andhra Pradesh (IN); Venkata Subbaraju Gottumukkala, Andhra Pradesh (IN); Venkateswarlu Somepalli, Andhra Pradesh (IN)

(73) Assignee: Laila Impex, Andhra Pradesh (IN)

( * ) Notice: Subject to any disclaimer, the term of this patent is extended or adjusted under 35 U.S.C. 154(b) by 725 days.

(21) Appl. No.: 10/541,828

(22) PCT Filed: Apr. 19, 2004

(86) PCT No.: PCT/IN2004/000107

§ 371 (c)(1),
(2), (4) Date: Jul. 12, 2005

(87) PCT Pub. No.: WO2005/099679

PCT Pub. Date: Oct. 27, 2005

(65) Prior Publication Data

US 2006/0106101 A1    May 18, 2006

(51) Int. Cl.
*A61K 31/19* (2006.01)
*C07C 59/245* (2006.01)
*C07C 59/265* (2006.01)

(52) U.S. Cl. .................. 514/574; 562/584; 562/582

(58) Field of Classification Search .................. None
See application file for complete search history.

(56) References Cited

U.S. PATENT DOCUMENTS

| 3,671,583 A | 6/1972 | Griot et al. |
| 5,536,516 A | 7/1996 | Moffett et al. |
| 5,626,849 A | 5/1997 | Hastings et al. |
| 6,160,172 A | 12/2000 | Balasubramanyam et al. |
| 6,221,901 B1 * | 4/2001 | Shrivastava et al. ......... 514/458 |

OTHER PUBLICATIONS

International Search Report mailed on Oct. 21, 2004.

* cited by examiner

*Primary Examiner*—Daniel M Sullivan
*Assistant Examiner*—Yevegeny Valenrod
(74) *Attorney, Agent, or Firm*—Rader, Fishman & Grauer PLLC

(57) ABSTRACT

This invention relates to new double salts of (−)-hydroxycitric acid with group II metals. Preferred double salts are calcium and magnesium double salts of hydroxycitric acid of the formula II. This invention also includes a process for the preparation of these double salts by the addition of one metal compound from group II to (−)-hydroxycitric acid solution followed by the addition of other metal compound solution from group II. These double salts are tasteless and are soluble in water. They are useful as dietary supplements and in beverages.

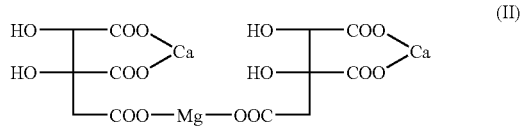

(II)

13 Claims, No Drawings

DOUBLE SALTS OF (−)-HYDROXYCITRIC ACID AND A PROCESS FOR PREPARING THE SAME

TECHNICAL FIELD OF THE INVENTION

This invention relates to new double salts of (−)-hydroxycitric acid with group II metals. Salts of particular importance are calcium and magnesium double salts of (−)-hydroxycitric acid. These double salts are useful nutraceuticals and dietary supplements. They are of particular relevance in beverage preparations.

BACKGROUND ART

The (−)-hydroxycitric acid (HCA) is a naturally occurring acid found in the fruit rind of *Garcinia* species. The dried fruit rind of *G. cambogia*, also known as Malabar tamarind, is commonly used in Southeast Asia (particularly southern India) as a food preservative, flavoring agent and carminative. The primary mechanism of action of (−)-HCA appears to be due to their action as a competitive inhibitor of the enzyme ATP-citrate lyase, which catalyzes the conversion of citrate and coenzyme A to oxaloacetate and acetyl coenzyme A (acetyl-CoA). Extensive experimental studies suggest that (−)-HCA suppresses the fatty acid synthesis, lipogenesis and food intake thus leading to weight reduction. In addition to suppression of fatty acid and fat synthesis, (−)-HCA is thought to suppress food intake through loss of appetite by stimulation of liver gluconeogenesis. Various researchers have evaluated HCA for its weight control properties, fat burning properties, lipid level lowering effect, appetite regulation, metabolic rate increase and other effects. A number of patents have been granted based on the above studies and various methods of extraction of HCA from the fruit. The isolation and chemical nature of (−)-hydroxycitric acid from *Garcinia* rind are described in the publication of Lewis, Y. S. et al, Phytochemistry, 1965, 4, 619-625. Moffett, et al., U.S. Pat. No. 5,656,314 (1997) described a process for the aqueous extraction of (−)-HCA from *Garcinia* rinds.

It has been found that the free acid form of (−)-hydroxycitric acid is unstable, forming a lactone (FIG. 1), which generally does not possess the desired bioactivity and also the liquid form of HCA tends to be unstable during storage. Therefore, food preparations that incorporate the free acid in liquid form will not provide the full benefit of the HCA in the final preparation.

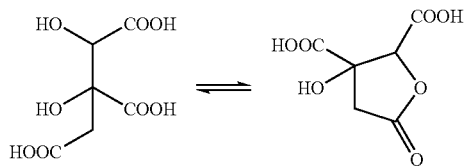

A number of patents have been granted for the preparation of (−)-hydroxycitric acid salts. Singh, et al., Biol. Memoirs, 1995, 21, 27-33, describes the preparation of calcium salt of HCA. The drawback of this salt is that it is not very soluble in water. Majeed, et al., U.S. Pat. No. 5,783,603 (1998), disclosed the preparation of potassium salt of HCA, but it is hygroscopic and has strong pungent taste. Ganga Raju, G. PCT Publication No. WO 99/03464 (28 Jan., 1999) described the preparation of calcium and potassium or sodium double salts of HCA and its use as dietary supplements and food products to reduce body weight. Balasubramanyam, et al., U.S. Pat. No. 6,160,172 (2000), disclosed the preparation of similar double salts of HCA.

Calcium gives bones their strength, while magnesium helps them maintain their elasticity to prevent injury. The more calcium in the diet, the more magnesium that is needed. Calcium given alone can induce a magnesium deficiency. The most serious complications from a deficiency of magnesium are heart conditions such as irregular heartbeat and rapid heartbeat (Bariscode, M. et al., American Journal of Nutrition, 1996, 19, 296). The magnesium dose recommended in USA by the Daily Reference Intake (DRI) is 420 mg for males and 330 mg for females. So it is good to have good calcium and magnesium in our daily diet or as food supplements. Shrivatstava, et al, U.S. Pat. No. 6,221,901 (2001) disclosed the use magnesium (−) hydroxycitrate as dietary nutritional supplement.

Zinc is an essential mineral that is found in almost every cell. It is needed for wound healing, sense of taste and smell, DNA synthesis and it supports normal growth and development during pregnancy, childhood and adolescence. The DRI's of zinc for adult male is 11 mg and for adult female is 8 mg.

There exits a need for a stable and water soluble (−)-hydroxycitric acid salts that overcome the above drawbacks of insolubility, pungent taste which additionally have many desired minerals for health benefit.

OBJECTS OF THE INVENTION

A stable water soluble salt of hydroxycitric acid of the general formula 1 shown below

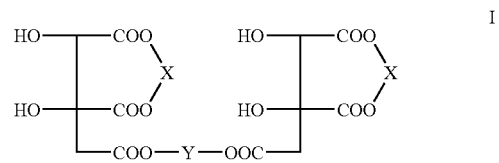

wherein X and Y are independently selected from metals of group II (II A & II B) of the Periodic Table.

This invention also relates to a process for preparing double salts of (−)-hydroxycitric acid of the above general formula which comprises the steps of adding a solution of a group II metal compound to an aqueous solution of (−)-hydroxycitric acid followed by the addition of another group II metal compound solution and recovering the double salt from the reaction mixture in a known manner.

DISCLOSURE OF THE INVENTION

New double salts of (−)-hydroxycitric acid of the general formula I

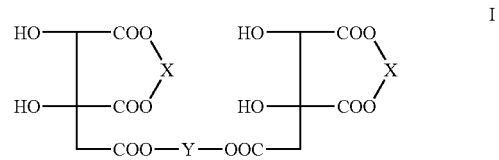

wherein X and Y are independently selected from group II metals of the Periodic Table are disclosed in this specification. Salts of particular relevance are calcium and magnesium or zinc double salts of (−)-hydroxycitric acid as shown in formula II.

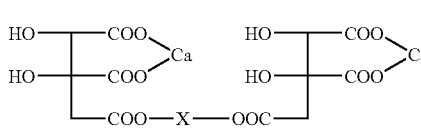

wherein X represents magnesium or zinc.

This invention also discloses a process for preparing the double salts of (−) hydroxycitric acid. This process comprises adding stoichiometric quantities of the desired compounds of group IIA metals to (−)-hydroxycitric acid. Slow addition of a group IIA metal compound or zinc compound to a purified aqueous extract of hydroxycitric acid followed by the addition of the other group IIA metal compound is a preferred process. An extract obtained from garcinia fruits may be made the source of HCA. In this process, purified (−)-hydroxycitric acid is prepared by treating the calcium hydroxycitrate obtained from water extract of the Garcinia fruit with phosphoric acid (Ganga Raju, G, PCT Publication No. WO 99/03464) or passing the water extract of the Garcinia fruit through anion exchange resin followed by passing through cation exchange column. This purified (−)-HCA is reacted with required quantities of a magnesium compound and a calcium compound. After charcoal treatment for purification, the salt is recovered by spray drying or the double salt is separated from the reaction mixture by adding water miscible solvents, like alcohols, acetone, acetonitrile, dioxan, tetrahydrofuran or mixtures thereof. Although the structure of the resultant product is not known with certainty, a likely structural formula for the preferred product is shown above (formula II).

Any water soluble metal compounds may be used in this process. Preferred compounds are carbonates and hydroxides of group II. Calcium and magnesium are the preferred metals. These double salts show water solubility and are tasteless when compared with the naturally occurring HCA. As such, these salts are excellent food supplements for essential minerals like calcium and magnesium. Furthermore, these salts provide the desired balance between the two minerals and enhance their assimilation in the small intestine.

Structural Analysis of the Calcium and Magnesium Double Salt of (−)-HCA

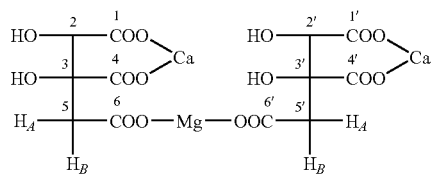

The structure of the calcium and magnesium double salt of (−)-HCA was confirmed by its $^1$H NMR and $^{13}$C NMR data. The $^1$H NMR signals (FIG. 2) of methylene protons ($H_A$-5, $H_A$-5' & $H_B$-5, $H_B$-5') appeared at δ2.54, 2.66 as two doublets with large coupling constants (16.6 Hz), characteristic of geminal protons and a singlet at δ3.97 corresponding to methine protons (H-2, H-2'; Table-1). In $^{13}$C NMR spectrum (FIG. 3) the peaks at δ42.31, 76.69 & 79.61 could be assigned to methylene carbons (C-5, C-5'), methine carbons (C-2, C-2') and quaternary carbons (C-3, C-3'), respectively. The peaks at δ178.54, 179.40 and 180.68 correspond to carbonyl carbons (C-1 & C-1', C-4 & C-4' and C-6 & C-6') of the carboxylate groups. Mass (ESI, negative scan): m/z 207 (M-H)$^-$. The metals, calcium and magnesium were estimated by EDTA-titrimetric method (Jeffery, G. H., Bassett, J., Mendham, J., Denney, R. C. in: Vogel's text book of Quantitative Chemical Analysis, Fifth Ed.; ELBS: UK, 1989). The analytical data of the representative salt was found to be calcium: 11.88% and magnesium: 5.73%.

TABLE 1

Proton NMR spectral data of calcium and magnesium double salt of (−)-HCA

| S. No: | δ H (D$_2$O) | Assignment |
| --- | --- | --- |
| 1 | 2.54 (d, J=16.6 Hz) | $H_A$-5,5' |
| 2 | 2.66 (d, J=16.6 Hz) | $H_B$-5,5' |
| 3 | 3.97(s) | H-2,2' |

TABLE 2

Carbon NMR spectral data of calcium and magnesium double salt of (−)-HCA

| S. No. | δ C (D$_2$O) | Assignment |
| --- | --- | --- |
| 1 | 42.31 | C-5,5' |
| 2 | 76.69 | C-2,2' |
| 3 | 79.61 | C-3,3' |
| 4 | 178.54, 179.40 and 180.68 | C-1,1' & C-4,4' & C-6,6' |

DESCRIPTION WITH REFERENCE TO PREFERRED EMBODIMENTS

Preferred embodiments relating to the different process of preparing the double salts of (−)-hydroxycitric acid of the subject invention are illustrated in the examples given below:

EXAMPLE: 1

Calcium and magnesium double salt of HCA: To an aqueous purified extract of garcinia solution (83 ml, 3.5 g) was added a solution of magnesium carbonate (0.9 g) in water (10 mL) and stirred for 0.5 h. Then a solution of calcium hydroxide (1.25 g) in water (50 mL) was added and after stirring for 1 h, the pH of the solution was adjusted to 9.4 using magnesium carbonate (0.5 g) and calcium hydroxide (0.5 g). The solution was stirred at 70-80° C. for 4 h. The solution was cooled and filtered and the solid obtained was dried to give a colourless calcium and magnesium double salt of HCA (4.8 g).

The analysis showed that (−)-HCA is 73.88%; lactone is 0.24%; calcium is 12.78% and magnesium is 2.50%.

EXAMPLE: 2

Calcium and magnesium double salt of HCA: To an aqueous purified extract of garcinia solution (332 ml, 14.0 g) was added a solution of magnesium carbonate (8.0 g) in water (50 mL) and stirred for 0.5 h. Then a solution of calcium hydroxide (4.8 g) in water (100 mL) was added and the solution was stirred at 70-80° C. for 4 h. The pH of the solution was adjusted to 7.5 using *garcinia* solution. Charcoal (5.0 g) was added and stirred at 70-80° C. for 1 h and filtered through celite. The solution was evaporated or spray dried to give a colourless calcium and magnesium double salt of HCA (13.0 g).

The analysis showed that (−)-HCA is 73.17%; lactone is 0.43%; calcium is 11.88% and magnesium is 5.73%.

EXAMPLE: 3

Magnesium and zinc double salt of HCA: To an aqueous purified extract of *garcinia* solution (83 ml, 3.5 g) was added a solution of magnesium carbonate (3.6 g) in water (20 mL) and stirred for 0.5 h. Then a solution of zinc carbonate (2.0 g) in water (50 mL) was added and the solution was stirred at 70-80° C. for 4 h. Charcoal (3.0 g) was added and stirred at 70-80° C. for 1 h and filtered through celite. The solution was evaporated to give a colourless magnesium and zinc double salt of HCA (5.0 g).

The analysis showed that (−)-HCA is 66.50%; lactone is 0.65%; magnesium is 8.5% and zinc is 9.5%.

EXAMPLE: 4

Calcium and zinc double salt of HCA: To an aqueous purified extract of *garcinia* solution (83 ml, 3.5 g) was added a solution of zinc carbonate (1.25 g) in water (20 mL) and stirred for 0.5 h. Charcoal (2.0 g) was added and stirred at 70-80° C. for 1 h and filtered through celite. Then a solution of calcium hydroxide (1.8 g) in water (50 mL) was added and the solution was stirred at 70-80° C. for 4 h. The solution was cooled and the precipitated solid was filtered and dried to give a colourless calcium and zinc double salt of HCA (5.0 g).

The analysis showed that (−)-HCA is 64.14%; lactone is 0.42%; calcium is 10.09% and zinc is 9.69%.

Preferred calcium and magnesium contents of the double salts are 5-20% calcium and 2-10% magnesium. Obvious equivalents and modifications known to persons skilled in the art are within the scope and ambit of the appended claims.

The invention claimed is:

1. Double salts of (−)-hydroxycitric acid (HCA) as shown in the general formula I

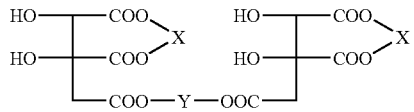

wherein X and Y are independently selected from metals of group II (IIA & IIB) of the Periodic Table, and wherein X is different from Y.

2. The double salts as claimed in claim 1, wherein the metals are group II metals and are independently selected from Be, Mg, Ca, Sr, Ba or Ra (group IIA), Zn, Cd or Hg (group IIB) in the form of their carbonates, oxides or hydroxides.

3. The calcium and magnesium double salt of (−)-HCA as claimed in claim 1, wherein X is calcium and Y is magnesium.

4. The calcium and zinc double salt of (−)-HCA as claimed in claim 1, wherein X is calcium and Y is zinc.

5. The magnesium and zinc double salt of (−)-HCA as claimed in claim 1, wherein X is magnesium and Y is zinc.

6. The double salt of HCA as claimed in claim 1, which is a calcium and magnesium double salt of the formula II wherein X = magnesium:

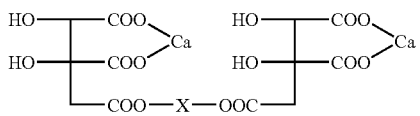

7. The double salt as claimed in claim 6, which has 20% by weight of calcium and 2-10% by weight of magnesium.

8. The calcium and magnesium double salt of (−)-HCA as claimed in claims 1 or 6, which has 50-80% by weight of HCA, 0-0.5% by weight of lactone, 5-16% by weight of calcium and 3-10% by weight of magnesium.

9. The calcium and zinc double salt of (−)-HCA as claimed in claim 1 or 4, which has 50-75% by weight of HCA, 0-0.5% by weight of lactone, 8-15% by weight of calcium and 5-12% by weight of zinc.

10. The magnesium and zinc double salt of (−)-HCA as claimed in claim 1 or 5, which has 50-80% by weight of HCA, 0-0.5% by weight of lactone, 5-10% by weight of magnesium and 5-15% by weight of zinc.

11. A method of 'reducing obesity' in mammals, wherein double salts of (−)-HCA as claimed in claim 1 are administered.

12. A method of treating 'osteoporosis', wherein double salts of (−)-HCA as claimed in claims 1 and 6 are administered.

13. The double salts of (−)-HCA as claimed in claim 1, for use in dietary or beverages or nutraceutical supplements.

* * * * *